(12) United States Patent
Granfors et al.

(10) Patent No.: US 7,558,412 B2
(45) Date of Patent: Jul. 7, 2009

(54) SYSTEM AND METHOD FOR COMPENSATION OF SCINTILLATOR HYSTERESIS IN X-RAY DETECTORS

(75) Inventors: Paul Richard Granfors, Sunnyvale, CA (US); Manat Maolinbay, Gilroy, CA (US); Richard Aufrichtig, Mountain View, CA (US)

(73) Assignee: General Electric Company, Schenectady, NY (US)

( * ) Notice: Subject to any disclaimer, the term of this patent is extended or adjusted under 35 U.S.C. 154(b) by 715 days.

(21) Appl. No.: 10/774,174

(22) Filed: Feb. 6, 2004

(65) Prior Publication Data

US 2005/0175254 A1 Aug. 11, 2005

(51) Int. Cl.
*G06K 9/00* (2006.01)

(52) U.S. Cl. .................. 382/128; 382/131; 382/275; 378/56; 378/98.8; 378/207; 378/201; 250/366; 250/311

(58) Field of Classification Search ............... 382/128, 382/131, 275; 250/363, 366, 370.9, 311, 250/370.09, 370.11; 378/108, 207, 201, 378/19, 98.8; 702/69, 88, 90, 109
See application file for complete search history.

(56) References Cited

U.S. PATENT DOCUMENTS

| | | | | |
|---|---|---|---|---|
| 4,586,068 A | * | 4/1986 | Petroff et al. ............... 257/438 |
| 5,760,403 A | * | 6/1998 | Elabd .................... 250/370.11 |
| 5,852,296 A | * | 12/1998 | Tsukamoto et al. .... 250/370.09 |
| 5,909,512 A | * | 6/1999 | Ohshima et al. ............ 382/251 |
| 6,404,853 B1 | * | 6/2002 | Odogba et al. ............. 378/98.8 |
| 6,438,201 B1 | * | 8/2002 | Mazess et al. ................ 378/56 |
| 6,460,003 B1 | * | 10/2002 | Kump et al. ................... 702/85 |
| 6,879,660 B2 | * | 4/2005 | Dhawale et al. ............ 378/98.8 |
| 6,996,262 B2 | * | 2/2006 | Li .............................. 382/131 |
| 7,260,174 B2 | * | 8/2007 | Hoffman et al. .............. 378/19 |
| 7,304,308 B2 | * | 12/2007 | Cheung et al. ......... 250/370.09 |
| 7,403,589 B1 | * | 7/2008 | Short et al. ................... 378/19 |
| 2002/0079458 A1 | * | 6/2002 | Zur ....................... 250/370.11 |
| 2003/0169850 A1 | * | 9/2003 | Kump et al. ................ 378/207 |
| 2004/0017224 A1 | * | 1/2004 | Tumer et al. .................. 327/51 |
| 2004/0217294 A1 | * | 11/2004 | Zur ....................... 250/370.09 |

* cited by examiner

*Primary Examiner*—Jingge Wu
*Assistant Examiner*—Nancy Bitar
(74) *Attorney, Agent, or Firm*—McAndrews, Held & Malloy, Ltd.; Peter J. Vogel; Michael A. Dellapenna (57) ABSTRACT

A method and system for detecting the potential of an x-ray imaging system to create images with scintillator hysteresis artifacts includes examining an x-ray image to measure two signal levels for two areas of interest, then determining a difference between the two signal levels and comparing the difference to a threshold. The signal levels can be measured by determining an amount of electrical charge discharged in photodiodes of the detector. If the difference in signals is greater than the threshold amount, then the possibility exists that scintillator hysteresis artifacts may be produced in images. In addition, the present invention also provides for the elimination or reduction in magnitude of scintillator hysteresis artifacts in images produced by an x-ray imaging system. After the possibility of scintillator hysteresis artifacts is detected, the detector can be irradiated with an x-ray flux to eliminate or reduce the magnitude of the artifacts in images produced by the x-ray imaging system.

22 Claims, 8 Drawing Sheets

SYSTEM AND METHOD FOR COMPENSATION OF SCINTILLATOR HYSTERESIS IN X-RAY DETECTORS

BACKGROUND OF THE INVENTION

The present invention relates generally to medical diagnostic imaging systems, and in particular relates to a system and method for the detection and compensation of scintillator hysteresis caused by electrical charge stored in charge trapping centers of scintillator material.

X-ray imaging has long been an accepted medical diagnostic tool. X-ray imaging systems are commonly used to capture, as examples, thoracic, cervical, spinal, cranial and abdominal images that often include information necessary for a physician to make an accurate diagnosis. X-ray imaging systems typically include an x-ray source and an x-ray detector. When having a thoracic x-ray image taken, for example, a patient stands with his or her chest against the x-ray sensor as an x-ray technologist positions the x-ray detector and the x-ray source at an appropriate height. X-rays produced by the source travel through the patient's chest, and the x-ray detector then detects the x-ray energy generated by the source and attenuated to various degrees by different parts of the body. An associated control system obtains the detected x-ray energy from the x-ray detector and prepares a corresponding diagnostic image on a display.

In addition, x-ray images may be used for many other purposes. For instance, internal defects in a target object may be detected. Additionally, changes in internal structure or alignment may be determined. Furthermore, the image may show the presence or absence of objects in the target. The information gained from x-ray imaging has applications in many fields other than medicine, including manufacturing.

The x-ray detector may be a conventional screen/film configuration, in which the screen converts the x-rays to light that exposes the film. The x-ray detector may also be a solid-state digital image detector. Digital detectors afford a significantly greater dynamic range than conventional screen/film configurations.

Figure 1:
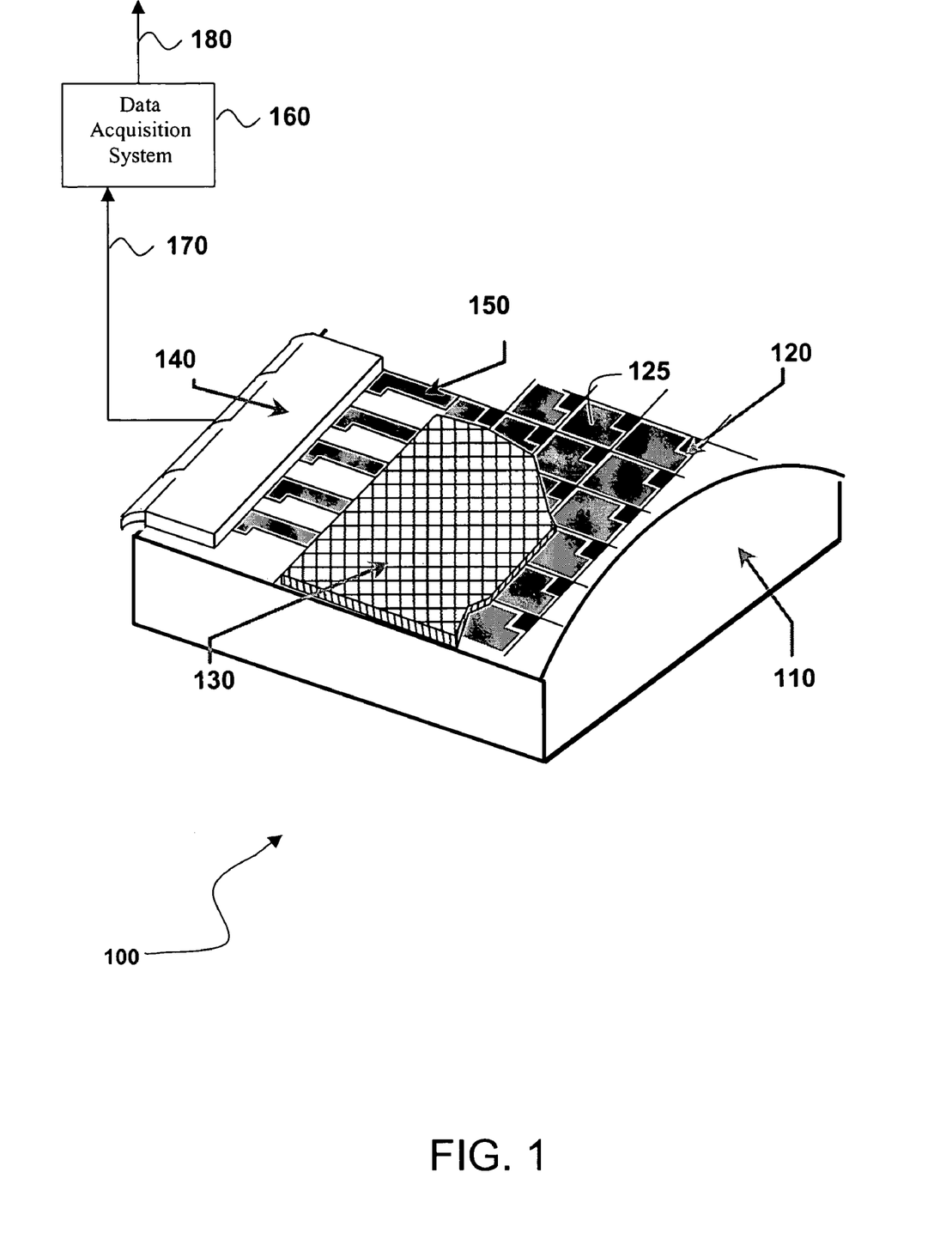
FIG. 1 illustrates an exemplary digital x-ray detector.

An exemplary digital x-ray detector is shown in FIG. 1. Digital detectors 100 generally include a substrate material 110, a matrix of picture elements 120, a scintillator 130, readout electronics 140 and electrical connects 150. The matrix of picture elements (pixels) 120 is placed between the substrate material 110 and the scintillator 130. The matrix of pixels 120 is electronically connected to the readout electronics 140 by the electrical connects 150. The matrix of pixels 120 includes multiple pixels. Each pixel typically includes a photodiode 125.

The scintillator 130 is composed of x-ray converter material that converts incident x-ray flux into light. An x-ray flux source directs x-ray flux to the detector 100. The x-ray flux then strikes the detector 100. When the x-ray flux strikes the detector 100, the scintillator 130 converts the x-ray flux into light. The light then passes down to the matrix of pixels 120. Each photodiode 125 is initially charged with a known amount of reverse bias voltage. Once the light strikes the photodiodes 125 contained in the matrix of pixels 120, the light discharges some or all of the stored reverse bias voltage. Photodiodes 125 that receive greater intensity of incident light discharge a greater amount of initially stored voltage than photodiodes 125 that receive a lesser intensity of incident light. In an x-ray imaging of a human bone, for example, denser areas of the human bone block more x-rays from striking the detector 100 than areas of the detector 100 where no human bone or less dense bone is present. Therefore, the area of the detector 100 under the denser areas of the bone receives less x-ray flux. A smaller amount of x-ray flux striking the detector 100 causes less x-ray flux to be converted into light by the scintillator 130. The decreased conversion of x-ray flux into light in turn causes less light to strike the matrix of pixels 120, and correspondingly, the photodiodes 125. With less light striking the photodiodes 125, less electrical charge is discharged from the photodiodes 125.

Conversely, in the areas of the detector 100 where there is a smaller density of human bone or no bone, less x-ray flux is blocked out and more x-ray flux strikes the scintillator 130. With a larger x-ray flux striking the scintillator 130, more x-ray flux is converted into light by the scintillator 130. Therefore, more light strikes the matrix of pixels 120, and correspondingly, the photodiodes 125. With more light striking the photodiodes 125, more electrical charge is discharged in the photodiodes 125.

The electrical charge stored in the photodiodes 125 is then read by the readout electronics 140. The readout electronics 140 scan the various pixels in the matrix of pixels 120 to determine the amount of initially stored electrical charge that has been discharged in the photodiodes 125, as described above. The readout electronics 140 convert the amount of discharged electrical charge in the photodiodes 125 into an image signal 170. In general, a large amount of discharged electrical charge in a photodiode 125 results in a high image signal 170 for the corresponding pixel. The image signal 170 is then sent to a data acquisition system 160. Once the data acquisition system 160 receives the image signal 170, the data acquisition system 160 uses the signal 170 to create an electronic x-ray image 180. The electronic x-ray image 180 may then be sent to an output, such as a computer screen.

Generally, photodiodes 125 and correspondingly, pixels, that receive greater intensities of incident light and therefore discharge a greater amount of electrical charge, have a large contrast with neighboring pixels that receive lesser intensities of incident light. The contrast in discharged electrical charge can cause sharp contrast in an x-ray image 180 between areas of the detector 100 where x-rays have struck the detector 100 unimpeded or by passing through objects with a lower density and areas of the detector 100 where x-rays were impeded in their path to the detector 100 by objects with a greater density.

In any imaging system, x-ray or otherwise, image quality is important. Image quality problems may be caused by electrical charge that has become stored, or "trapped," in areas of the scintillator 130. The trapped charge fills up the trapping centers in the scintillator 130, which can result in an increase of the image signal 170 per exposure, or gain of the scintillator 130. The increase of the gain of the scintillator 130, known as hysteresis, leads to an increase in image signal 170 for constant x-ray exposure.

Hysteresis can result from a large x-ray flux dose, such as 100 mR, to the scintillator 130. In addition, the scintillator 130 material may contribute to hysteresis. For example, scintillators 130 including CsI doped with Tl ("CsI(Tl)") generally contain deep charge trapping centers. The trapping centers may maintain or "trap" an electrical charge for an extended period of time. The trapped electric charges can cause an increase in the gain in the scintillator 130 and therefore an increase in the image signals 170. As discussed below, an increase in the image signals 170 may result in a shape artifact in the image 180. Gradually, the trapped electrical charge eventually decays enough to avoid significant imaging problems.

However, the deeper a charge-trapping center is, the longer the trapped charge takes to sufficiently decay. For example, the deep charge trapping centers of CsI(Tl) scintillators 130 can cause the decay time for the trapped electrical charges to be a considerably long time. When a significant number of deep charge trapping centers trap a sufficiently large electrical charge, a gain of the scintillator 130 and the image signal 170 can increase for the areas of the scintillator 130 where the deep charge trapping centers are filled with charge. Therefore, a uniform x-ray exposure to the detector 100 may cause increased signal 170 levels in areas with trapped charge. These areas of increased signal 170 levels may appear in images 180 as "ghosts" of previous x-ray exposures and are therefore referred to as "ghost images," or shape artifacts.

Figure 2:
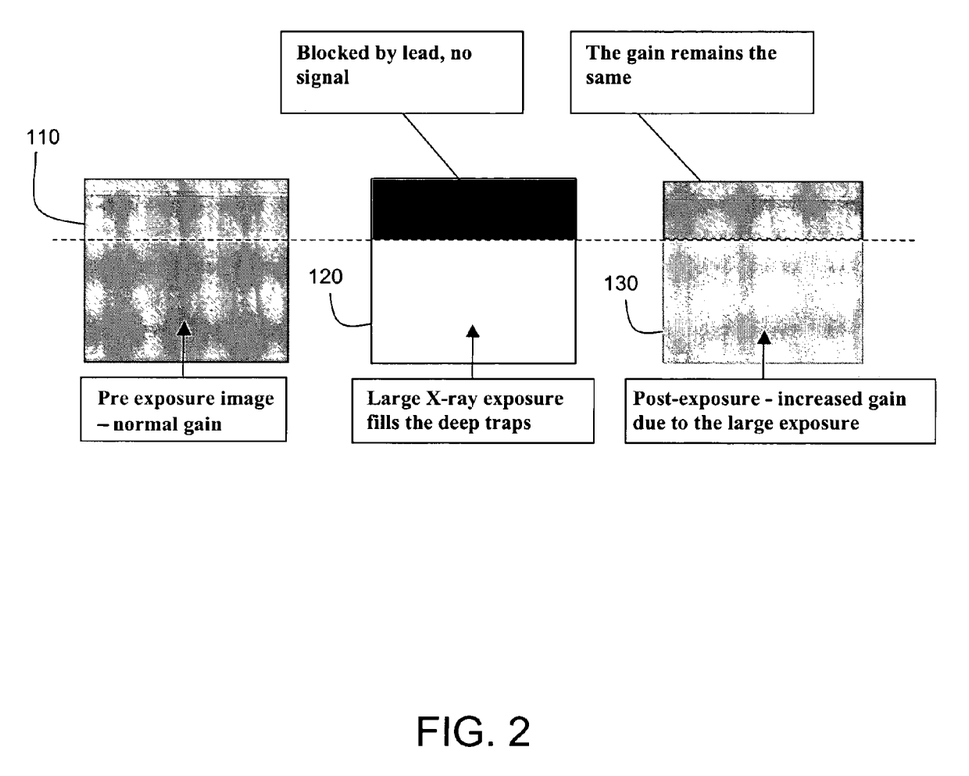
FIG. 2 illustrates images from an exemplary detector for a uniform exposure preceding a large non-uniform exposure, for a large non-uniform exposure and for a uniform exposure following the large non-uniform exposure.

Effects of hysteresis in an x-ray image 180 are exemplified in FIG. 2. FIG. 2 illustrates images 180 from an exemplary detector 100 for 1) a uniform exposure preceding a large non-uniform exposure (image 110), 2) for a large non-uniform exposure (image 120) and 3) for a uniform exposure following the large non-uniform exposure (image 130). For image 110, charge trap centers of the scintillator 130 in the detector 100 have little or no stored charge (that is, a scintillator 130 with normal gain). As discussed above, with little or no trapped charge in the charge trapping centers of the scintillator 130, an image signal 170 may not be affected, and the resultant signal level for the detector 100 appears uniform.

For image 120, the image 180 of a large non-uniform exposure, a top third of the detector 100 is covered with a lead sheet while a bottom two-thirds of the detector 100 is left uncovered. The detector 100 is then exposed to a large x-ray flux dose, for example 100 mR. The lead sheet over the top third of the detector 100 blocks the x-ray flux from striking the detector 100. Accordingly, the x-ray flux is blocked from striking the scintillator 130; and no x-ray flux is converted into light. Therefore, the photodiodes 125 in the top third of the detector 100 do not have any of their initial reverse bias voltage charge discharged by the light. When the readout electronics 140 scan the photodiodes 125, the readout electronics 140 create an image signal 170 that has no x-ray exposure for the photodiodes 125 in the top third of the detector 100. Therefore, when the image signal 170 is converted into the image 120, the top third of the detector 100 appears to be dark, indicating that the top third of the detector 100 was not exposed to an x-ray flux.

Conversely, in the bottom two-thirds of the detector 100 in image 120, a large x-ray flux dose strikes the detector 100, a large dose of x-ray flux strikes the scintillator 130 and a large dose of x-ray flux is converted into light. Therefore, the photodiodes 125 in the bottom two-thirds of the detector 100 discharge a large amount of stored electrical charge. Therefore, the photodiodes 125 in the bottom two-thirds of the detector 100 have a large amount of their initial reverse bias voltage charge discharged by the light. When the readout electronics 140 scan the photodiodes 125 to determine the electrical charge discharged in the photodiodes 125, the readout electronics 140 create an image signal 170 that has a large amount of x-ray exposure for the photodiodes 125 in the bottom two-thirds of the detector 100. Therefore, when the image signals 170 are converted into the image 120, the bottom two-thirds of the detector 100 appear to be bright, indicating that the bottom two-thirds of the detector 100 were exposed to a large amount of x-ray flux.

After waiting an amount of time so that all the electrical charge stored in the photodiodes 125 should be dissipated, the detector 100 may again be exposed to a uniform amount of x-ray flux to produce image 130. The amount of x-ray flux used to produce image 130 can be equivalent to the exposure level used in the first image 110. The readout electronics 140 then scan the photodiodes 125 to detect the amount of electrical charge discharged. Because the x-ray exposure was uniform and equal to that used to obtain the first image, the image signals 170 created by the readout electronics 140 should be uniform across the entire image 130 and display the same signal 170 levels as the image 110 taken prior to the large exposure. That is, as there has been no impedance to the uniform x-ray exposure used to produce either image 110 or image 130, both image 110 and image 130 should appear similar. However, the image signals 170 in image 130 are affected by changes in the scintillator 130 caused by the large nonuniform exposure. That is, as discussed above, a large x-ray flux may cause electrical charges to become trapped in the charge trapping centers of the scintillator 130 in the bottom two thirds of the detector 100; therefore, when the readout electronics 140 scan the detector 100, the bottom two-thirds of the detector 100 may have an increased signal 170. The image signal 170 from the bottom two-thirds of the detector 100 is sent to the data acquisition system 160 and appears in the image 130 as an area of increased signal 170.

Figure 3:
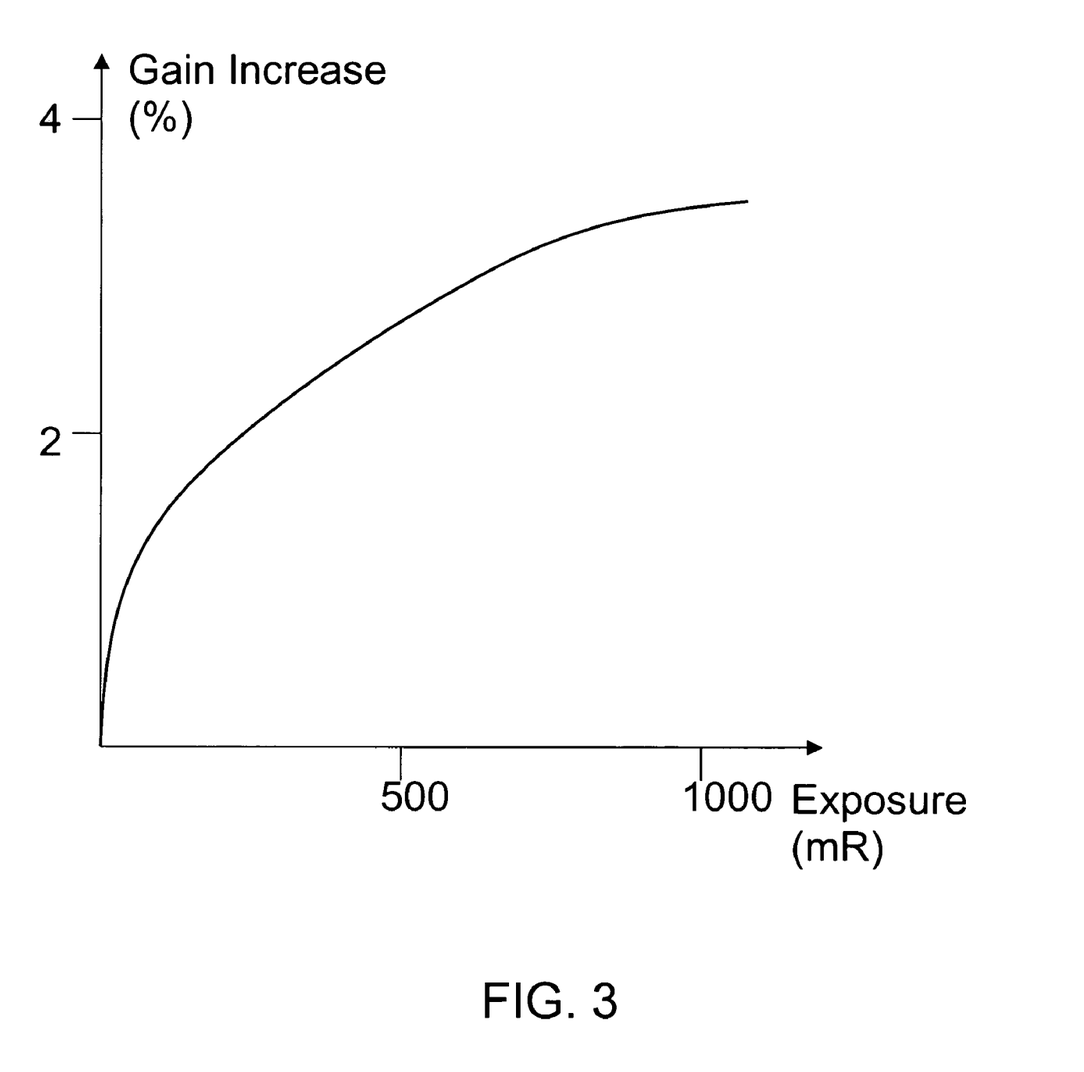
FIG. 3 illustrates a graph representing the relationship between an x-ray flux exposure and the increase in gain of a scintillator.

FIG. 3 illustrates a graph representing the relationship between an x-ray flux exposure and the increase in gain of a scintillator. The percentage increase in gain of the scintillator 130 represents the increase in gain of exposed portions of the scintillator 130 compared to the gain of unexposed portions of the scintillator 130. As FIG. 3 demonstrates, scintillator 130 hysteresis may cause a significant increase in gain of the scintillator 130. For example, FIG. 3 illustrates that an x-ray exposure may result in an increase in scintillator 130 gain of a few percent.

The shape artifacts or "ghost images" caused by scintillator 130 hysteresis are impediments to the image quality of x-ray images 180. For example, shape artifacts can appear to be non-existent objects in the x-ray image 180. In addition, the artifacts can effectively block or mask the appearance of an object of interest in an x-ray image 180. For example, an artifact may block or mask a tumor in the x-ray image 180 of the human anatomy.

Currently, no known solution exists for correcting scintillator 130 hysteresis. Possible solutions include either altering the material properties of the scintillator 130 or simply waiting for the electrical charge trapped in the charge trapping centers of the scintillator 130 material to decay. Changing the material properties of the scintillator 130 may include changing growth processes of the scintillator 130 material, altering the doping procedures of the dopant in the scintillator 130 and/or changing a microstructure of the scintillator 130. However, each of the proposed solutions is unlikely due to the high cost associated with altering material properties of the scintillator 130. In addition, altering material properties is an uncertain solution for correcting scintillator 130 hysteresis. Altering material properties is not known to definitively prevent or reduce scintillator 130 hysteresis while maintaining high x-ray image 180 quality. Also, as described above, simply "waiting out" the effects of scintillator 130 hysteresis in current systems by waiting until the trapped charges in the charge trapping centers of the scintillator 130 material have sufficiently decayed is an unrealistic solution as some trapped charges may require a considerable amount of time to sufficiently decay.

Therefore, a need currently exists for a method and system for detecting shape artifacts in an x-ray image caused by scintillator hysteresis and for minimizing or eliminating the shape artifacts caused by scintillator hysteresis.

BRIEF SUMMARY OF THE INVENTION

The present invention provides a method and system for detecting shape artifacts in an x-ray image caused by scintillator hysteresis and for minimizing or eliminating the shape artifacts. The method includes examining an image from a detector to measure two signal levels, determining a difference between the two signal levels and comparing this difference to a threshold. One signal level corresponds to a first area of interest in the image and the second signal level corresponds to a second area of interest in the image. Alternatively, the detector may first be exposed to a flat field x-ray exposure to produce the image. Furthermore, the threshold may alternatively be a percentage of an average of standard deviations of image signals from the two areas of interest. In addition, the method alternatively may irradiate the detector with an x-ray flux when the difference between the two signal levels is greater than the threshold.

The system of the present invention includes an x-ray image, readout electronics and a data acquisition system. The image includes two areas of interest. Each area of interest has a signal level. The readout electronics measure the two signal levels from the two areas of interest. The data acquisition system determines a difference between the two signals and compares this difference to a threshold.

Alternatively, the system may additionally include an x-ray detector that is exposed to a flat field x-ray exposure to produce the image. Furthermore, the threshold may alternatively be a percentage of an average of standard deviations of image signals. In addition, the system may alternatively further include an x-ray flux source that irradiates the detector with a second x-ray flux when the difference between the signal levels is greater than the threshold.

Another method of the present invention provides for the detection of differences in x-ray image signal levels. The method includes receiving two signals for an x-ray image, computing a difference between the two signals and notifying a user of an x-ray system when the difference is greater than a threshold. The two signals represent amounts of electrical charge measured in two areas of an x-ray detector. Alternatively, the method further includes exposing an x-ray detector to an x-ray flux if the difference is greater than the threshold, where the two signals are obtained from the detector.

DETAILED DESCRIPTION OF THE INVENTION

Figure 4:
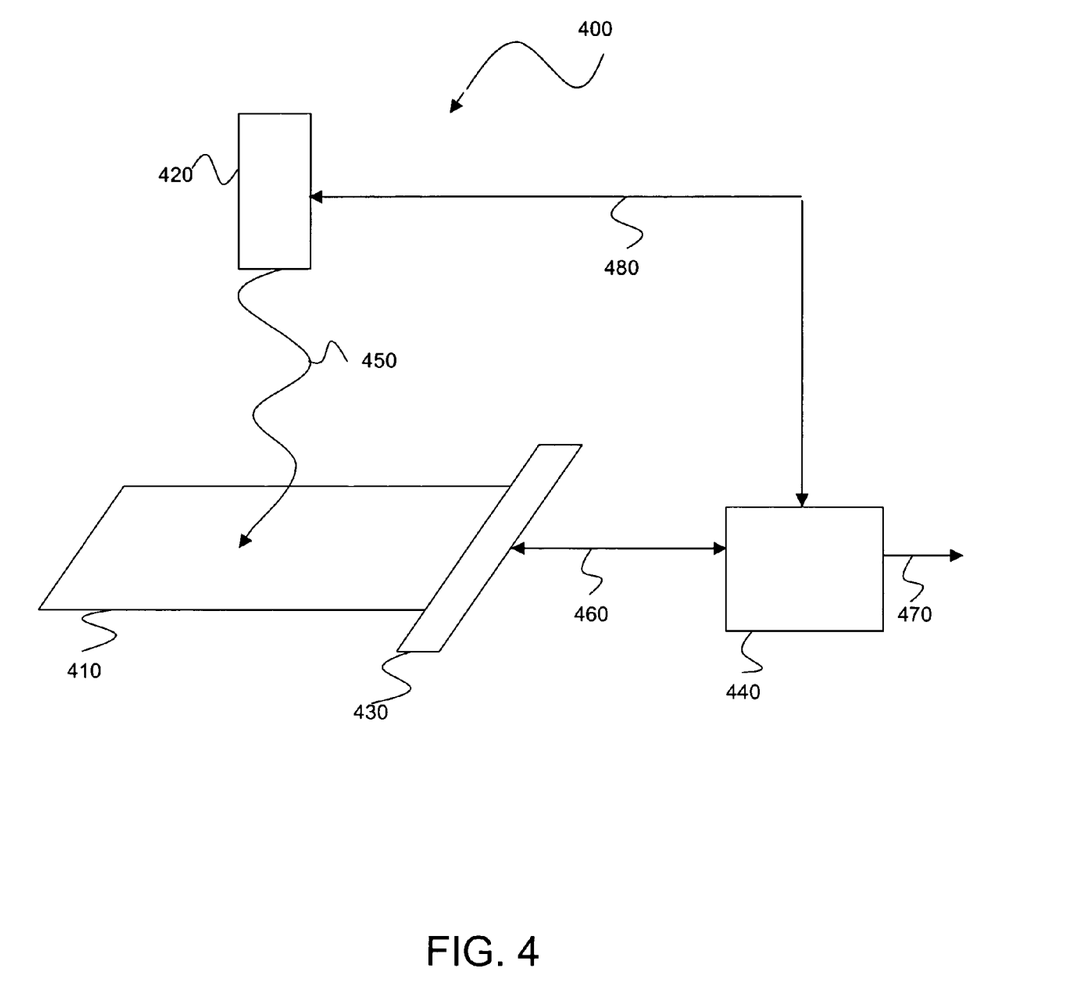
FIG. 4 illustrates an embodiment of a scintillator hysteresis detection system used in accordance with an embodiment of the present invention.

FIG. 4 illustrates an embodiment of a scintillator hysteresis detection system 400 used in accordance with an embodiment of the present invention. The detection system 400 includes a digital x-ray detector 410, an x-ray flux source 420, an electronic readout 430 and a data acquisition system 440. The x-ray flux source 420 generates an x-ray flux 450 in the direction of the detector 410. The electronic readout 430 is electrically connected to the detector 410 and to the data acquisition system 440. The electronic readout 430 sends image signals 460 to the data acquisition system 440. The data acquisition system 440 creates an x-ray image 470. The data acquisition system 440 sends exposure communication 480 to the x-ray source 420.

Figure 5:
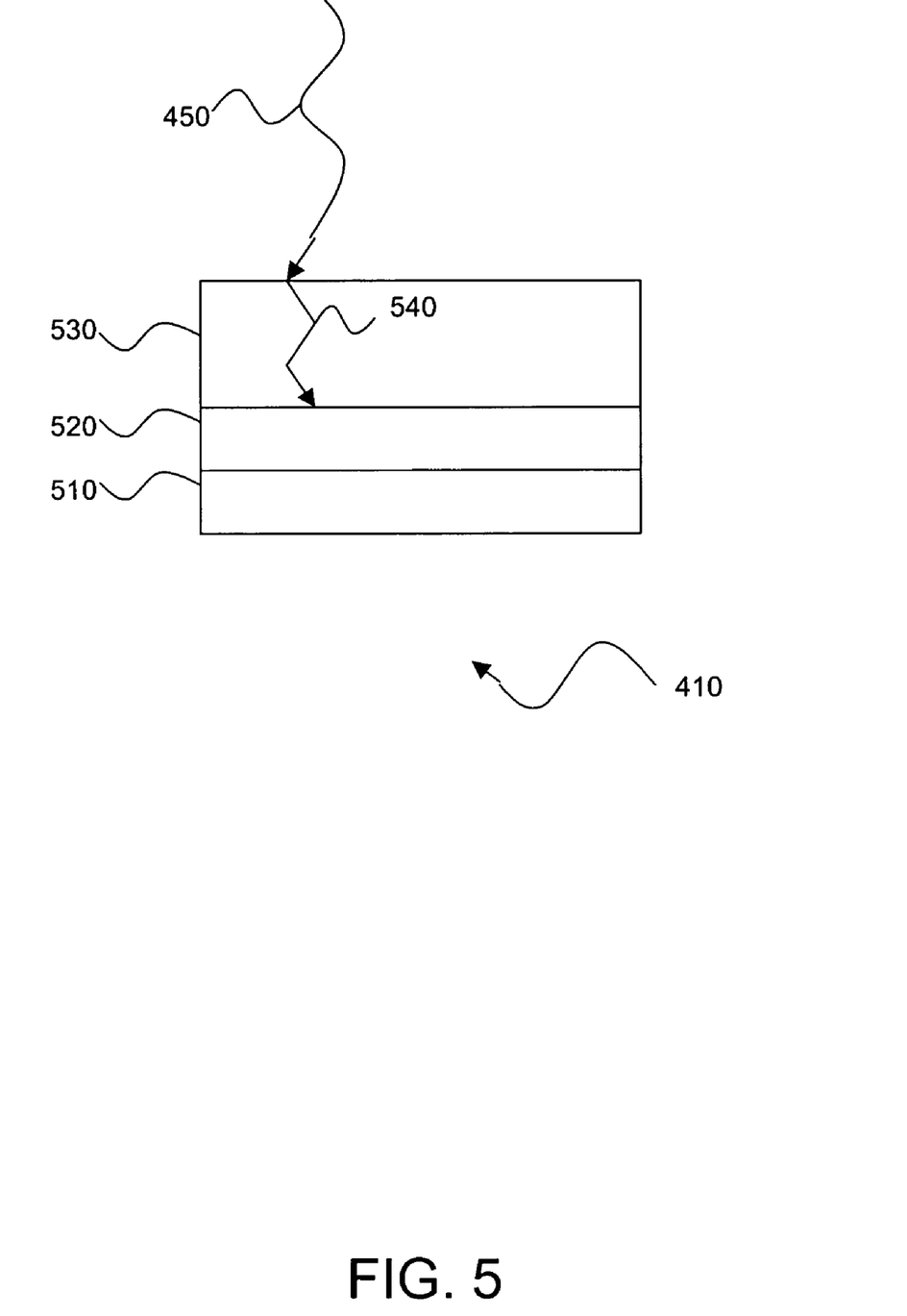
FIG. 5 illustrates an exemplary digital x-ray detector used in accordance with an embodiment of the present invention.

In an embodiment of the present system, the x-ray flux source 420 generates the x-ray flux 450 in the direction of the detector 410. The x-ray flux 450 strikes the detector 410. FIG. 5 illustrates an exemplary digital x-ray detector 410 used in accordance with an embodiment of the present invention. The detector 410 includes a substrate 510, a matrix of picture elements (pixels) 520 and a scintillator 530. The matrix of pixels 520 is located between the substrate 510 and the scintillator 530. The substrate 510 may include glass, for example. The matrix of pixels 520 includes an array of pixels, with each pixel including a photodiode and an associated thin film transistor ("TFT") switch. The scintillator 530 is typically composed of x-ray converter material. The x-ray converter material converts incident x-ray flux into light. In an embodiment, the scintillator 530 includes CsI(Tl).

As discussed above, in the operation of an exemplary detector 410, incident x-ray flux 450 strikes the scintillator 530. The scintillator 530 converts the incident x-ray flux 450 into light 540. The light 540 strikes the matrix of pixels 520.

Each photodiode in the pixels of the matrix of pixels 520 is initially charged with a known amount of reverse bias voltage, as discussed above. When the incident light 540 strikes the photodiodes, the light 540 discharges some or all of the reverse bias voltage stored by the photodiodes. The amount of voltage discharged in the photodiodes is preferably proportional to the intensity of the incident light 540. As the intensity of the incident light 540 is proportional to the intensity of the incident x-rays 450, the amount of voltage discharged in the photodiodes is therefore proportional to the intensity of the incident x-rays 450.

The electronic readout 430 then scans the pixels in the matrix of pixels 520 of the detector 410 to determine the amount of electric charge needed to restore the reverse bias voltage initially stored by the various photodiodes. That is, the electronic readout 430 determines how much of the initial reverse bias voltage that each photodiode is initially charged with (as described above) has been discharged by the incident light 540.

The scan by the electronic readout 430 results in image signals 460 being created. The image signals 460 generally include signal data for pixel elements in the matrix of pixels 520. That is, for each pixel element in the matrix of pixels 520, the image signals 460 include an amount of signal. Generally, the amount of signal is proportional to an amount of x-ray exposure experienced by the pixel in an ideal detector 410. The electronic readout 430 then sends the image signals 460 to the data acquisition system 440.

After receiving the image signals 460, the data acquisition system 440 examines the image signals 460 to create an x-ray image 470. The image 470 is created by analyzing the image signals 460 to determine the amount of x-ray exposure experienced by the various pixels in the matrix of pixels 520.

Consequently, in an embodiment of the present system, the data acquisition system 440 makes an area of the x-ray image 470 brighter for pixels that receive larger amounts x-ray flux 450 converted into light 540 than for pixels that receive smaller amounts of x-ray flux 450 converted into light 540.

For example, in an x-ray exposure of a human hand, the hand is placed between the x-ray flux source 420 and the detector 410. X-rays 450 incident on the hand result in complete or partial blockage of the x-rays 450, depending on the density of various areas of the hand. That is, x-rays 450 striking very dense portions of the bones in the hand are effectively blocked and the incident intensity of the x-rays 450 is greatly decreased. Conversely, x-rays 450 striking less dense portions of the hand, or missing the hand completely strike the detector 410 with little or no decrease in the incident intensity of the x-rays 450.

As the high and low incident intensity x-rays 450 strike the scintillator 530, the high and low incident intensity x-rays 450 are converted into high and low incident intensity light 540, respectively. The high and low incident intensity light 540 then strike the photodiodes in the pixels of the matrix of pixels 520.

The data acquisition system 440 receives the image signals 460 and converts the image signals 460 into the x-ray image 470. The image 470 may, for example, have brighter areas for the areas of the detector 410 (and corresponding pixels and photodiodes) that received larger incident intensity of light 540 than the areas of the detector 410 (and corresponding pixels and photodiodes) that received smaller incident intensity of light 540.

However, as discussed above, portions of the scintillator 530 that experience the effects of hysteresis (namely, increased gain of the scintillator 530) can cause an increase in the image signals 460. The increase in gain is not a result of an actual change in x-ray flux 450, but is a result of the increased gain of the scintillator 530. As discussed above, the increase in scintillator 530 gain can slowly decay to an original, pre-exposure scintillator 530 gain level.

In order to detect scintillator 530 hysteresis, and therefore the possibility of shape artifacts appearing in the image 470, the detector 410 is irradiated with a uniform field of x-rays 450. The electronic readout 430 then collects the stored electric charge data and creates the image signals 460 for the detector 410, as described above. The image signals 460 are then sent to the data acquisition system 440. After the data acquisition system 440 receives the image signals 460, the data acquisition system 440 may divide the image signals 460 into two or more regions of interest ("ROI"). An ROI is a set of pixels in the matrix of pixels 520. For example, an ROI may be a set of the matrix of pixels 520 defined as 50 pixels by 50 pixels, or 100 pixels by 100 pixels.

The data acquisition system 440 then computes a contrast-to-noise ratio ("CNR") of image signals 460 for one or more pairs of neighboring ROIs. As discussed above, the image signals 460 generally include signal data for each pixel element in the matrix of pixels 520. The CNR may be understood to be a signal-difference-to-noise ratio that relates to the difference in image signals 460 between two ROIs. The data acquisition system 440 determines if the possibility of a shape artifact appearing in the image 470 exists by comparing the CNR of at least two ROIs to a threshold. A figure of merit may be defined by the system 400 as the maximum CNR between any two neighboring ROIs. The figure of merit may be defined mathematically as:

$$CNR_{max} = \max\left\{\frac{|\mu_{i1} - \mu_{i2}|}{\frac{1}{2}(\sigma_{i1} + \sigma_{i2})}\right\} \times 100\% \quad (1)$$

where $\mu_{i1}$ and $\mu_{i2}$ are average image signals 460 and $\sigma_{i1}$ and $\sigma_{i2}$ are standard deviations of image signals 460 within at least two neighboring ROIs (namely, $ROI_{i1}$ and $ROI_{i2}$). The index "i" runs over ails pairs of ROIs ($ROI_{i1}$ and $ROI_{i2}$) that are used for the calculation. $CNR_{max}$ is determined from the maximum (max) of the quantity in braces over all pairs of ROIs used for the calculation. If $CNR_{max}$ exceeds some threshold $CNR_T$ (the "visibility threshold"), then this is an indication that the detector 410 could produce x-ray images 470 with shape artifacts.

In general, a shape artifact may be visible in the image 470 to the human eye when $CNR_{max}$ exceeds $CNR_T=40\%$, for example. Therefore, in one embodiment of the present system, the data acquisition system 440 determines that a shape artifact could be visible when $CNR_{max}$ exceeds 40%. However, the visibility threshold $CNR_T$ may be customized by the user, as described below.

Once the data acquisition system 440 recognizes that a shape artifact could be visible, a notification is made to the user of the scintillator hysteresis detection system 400. The notification may exist, for example, as an audible alarm or a visible warning or error message on an output of the data acquisition system 440.

Once the possibility of a shape artifact appearing in the image 470 has been detected by the data acquisition system 440, the scintillator hysteresis detection system 400 may then attempt to reduce or eliminate the shape artifacts. The shape artifacts may be minimized or eliminated by "bleaching" the detector 410. "Bleaching" is an irradiation of the detector 410 with a flat field x-ray flux 450. The "bleaching" of a detector 410 with scintillator 530 hysteresis artifacts may be repeated several times in order to sufficiently reduce or eliminate the scintillator 530 hysteresis artifacts.

In operation, if the possibility of a shape artifact appearing in the image 470 is discovered in the detector 410, as described above, the data acquisition system 440 may send an exposure communication 480 to the x-ray flux source 420, as shown in FIG. 4. The exposure communication 480 may include two items of information to be communicated to the x-ray flux source 420. First, the exposure communication 480 may include a command to the x-ray flux source 420 to "bleach," or irradiate, the detector 410 with a flat field x-ray flux 450. Second, the exposure communication 480 may include information as to the intensity of the flat field x-ray flux 450 to be used in the "bleaching" of the detector 410.

The data acquisition system 440 preferably sends the exposure communication 480 to the x-ray flux source 420 automatically. That is, as described above, as soon as the data acquisition system 440 determines that a possibility of a shape artifact appearing in the image 470 exists, the data acquisition system 440 sends exposure communication 480 to the x-ray flux source 420.

The intensity of the flat field x-ray flux 450 used to "bleach" the detector 410 may typically be about the same as the x-ray flux 450 intensity that was used in initially causing the scintillator 530 hysteresis. That is, if an x-ray image 470 is taken of an object using an x-ray flux 450 intensity of 100 mR, and a possibility of a shape artifact appearing in the image 470 is discovered by the data acquisition system 440, the data acquisition system 440 sends exposure communication 480 directing the x-ray flux source 420 to "bleach" the detector 410 with a flat field x-ray flux 450 with an intensity of about 100 mR.

After the data acquisition system 440 sends exposure communication 480 to the x-ray flux source 420 and the x-ray flux source 420 has "bleached" the detector 410, the scintillator hysteresis detection system 400 attempts to detect the remaining possibility of shape artifacts appearing in the image 470. If the data acquisition system 440 does detect a remaining possibility, the data acquisition system 440 sends another exposure communication 480 to the x-ray flux source 420. That is, the scintillator hysteresis detection system 400 loops through the process of exposing the detector 410 to a flat field x-ray dose, detecting the possibility of shape artifacts appearing in the image 470 and "bleaching" the detector 410. This loop may continue until $CNR_{max}$ has been decreased below the visibility threshold (for example 40%, as described above).

Figure 6:
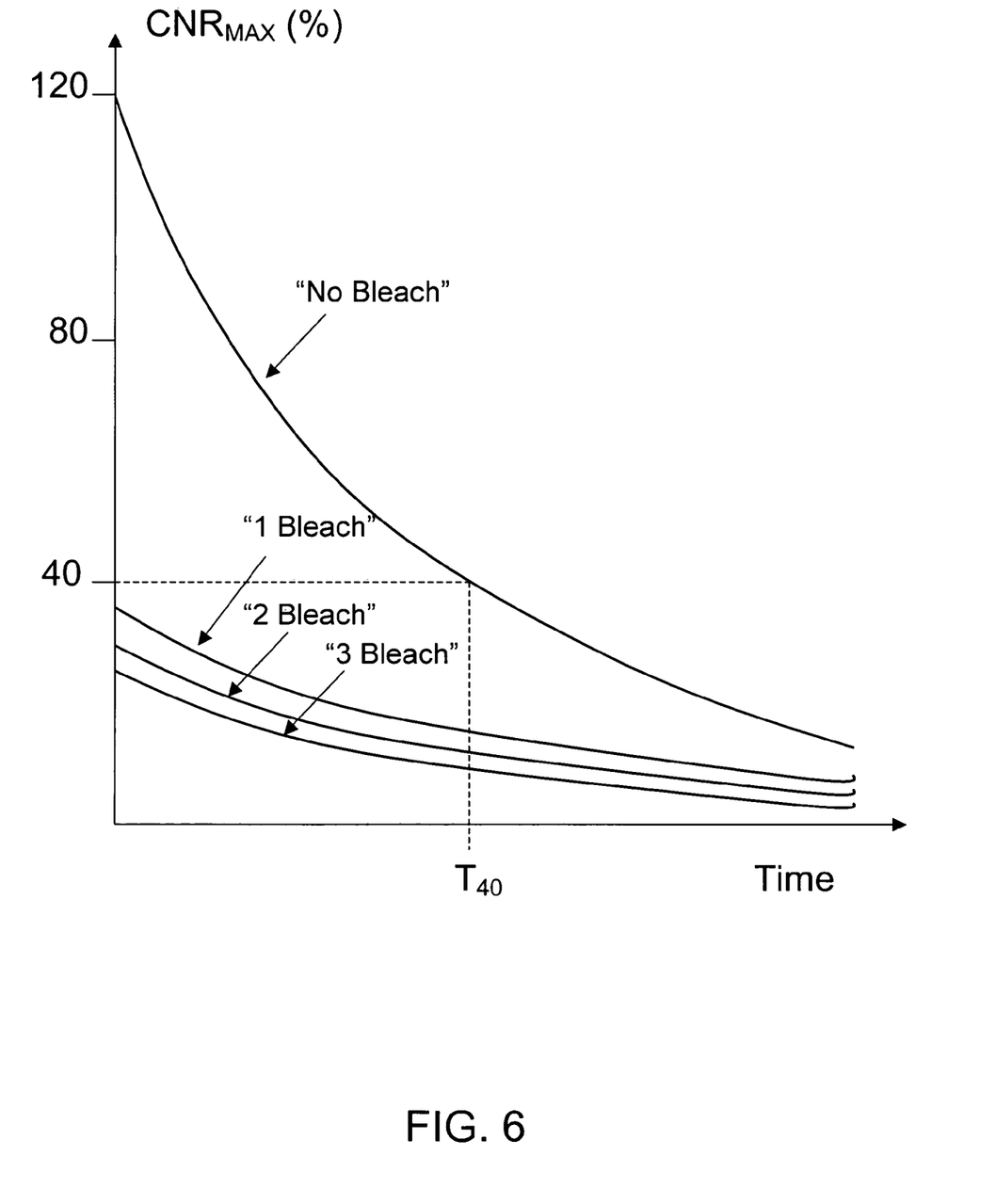
FIG. 6 illustrates a graphical representation of the operation of the scintillator hysteresis detection system in accordance with an embodiment of the present invention.

FIG. 6 is a graphical representation of the operation of the scintillator hysteresis detection system 400. The curve marked "No bleach" represents the $CNR_{max}$ of an image from a detector 410 taken over a period of time without any "bleaching" of the detector 410, as described above. That is, the "No bleach" curve represents an x-ray system that does not employ the use of the scintillator hysteresis detection system 400 and does not attempt to eliminate or reduce any discovered shape artifacts.

In an embodiment, a $CNR_{max}$ greater than $CNR_T$=40% is an indication that a shape artifact could be visible to the human eye. Therefore, the curve designated by "No bleach" in FIG. 6 represents a situation where shape artifacts could be visible for a time period $T_{40}$ during which the $CNR_{max}$ is above 40%. Alternatively, if a threshold of $CNR_T$=50% is used, a shape artifact may be visible for a shorter duration than $T_{40}$, while the curve marked "No bleach" remains above a $CNR_{max}$ of 50%.

Conversely, the remaining three curves in FIG. 6 designated as "1 bleach," "2 bleach" and "3 bleach" represent the $CNR_{max}$ of an image 470 from a detector 410 over a period of time with "bleaching" of the detector 410, as described above. That is, as opposed to the previous discussion, the curves represent an x-ray system that has detected the possibility of shape artifacts and is now "bleaching" the detector 410 with a flat field x-ray dose 450.

The curve designated "1 bleach" represents the $CNR_{max}$ of an image 470 from a detector 410 that has been "bleached" once with a flat field x-ray flux 450 dose of 100 mR, for example. The curve designated "2 bleach" represents the $CNR_{max}$ of an image 470 from a detector 410 that has been "bleached" twice with a flat field x-ray flux 450 dose of 100 mR, for example. The curve designated "3 bleach" represents the $CNR_{max}$ of an image 470 from a detector 410 that has been "bleached" three times with a flat field x-ray flux 450 dose of 100 mR, for example.

As previously stated, a $CNR_{max}$ above a $CNR_T$ of 40%, for example, may be representative of a situation in which a shape artifact may be visible to the human eye. Therefore, no shape artifact should be visible in images from the detector represented in FIG. 6 after a single "bleaching" of the detector 410. That is, after a single "bleach" of the detector 410 with a flat field x-ray flux 450 dose of 100 mR, for example, the $CNR_{max}$ of the image 470 decreases to below the $CNR_{max}$ visibility threshold, $CNR_T$. Similarly, after a second or third "bleach," the $CNR_{max}$ of the image 470 may be further reduced. Therefore, after the possibility for the detector 410 to produce images 470 with shape artifacts is discovered by the data acquisition system 440, the possibility of a shape artifact appearing in the image 470 may be reduced or eliminated by a singular or multiple iterations of a "bleaching" of the detector 410 with a flat field x-ray flux 450, for example.

Figure 7:
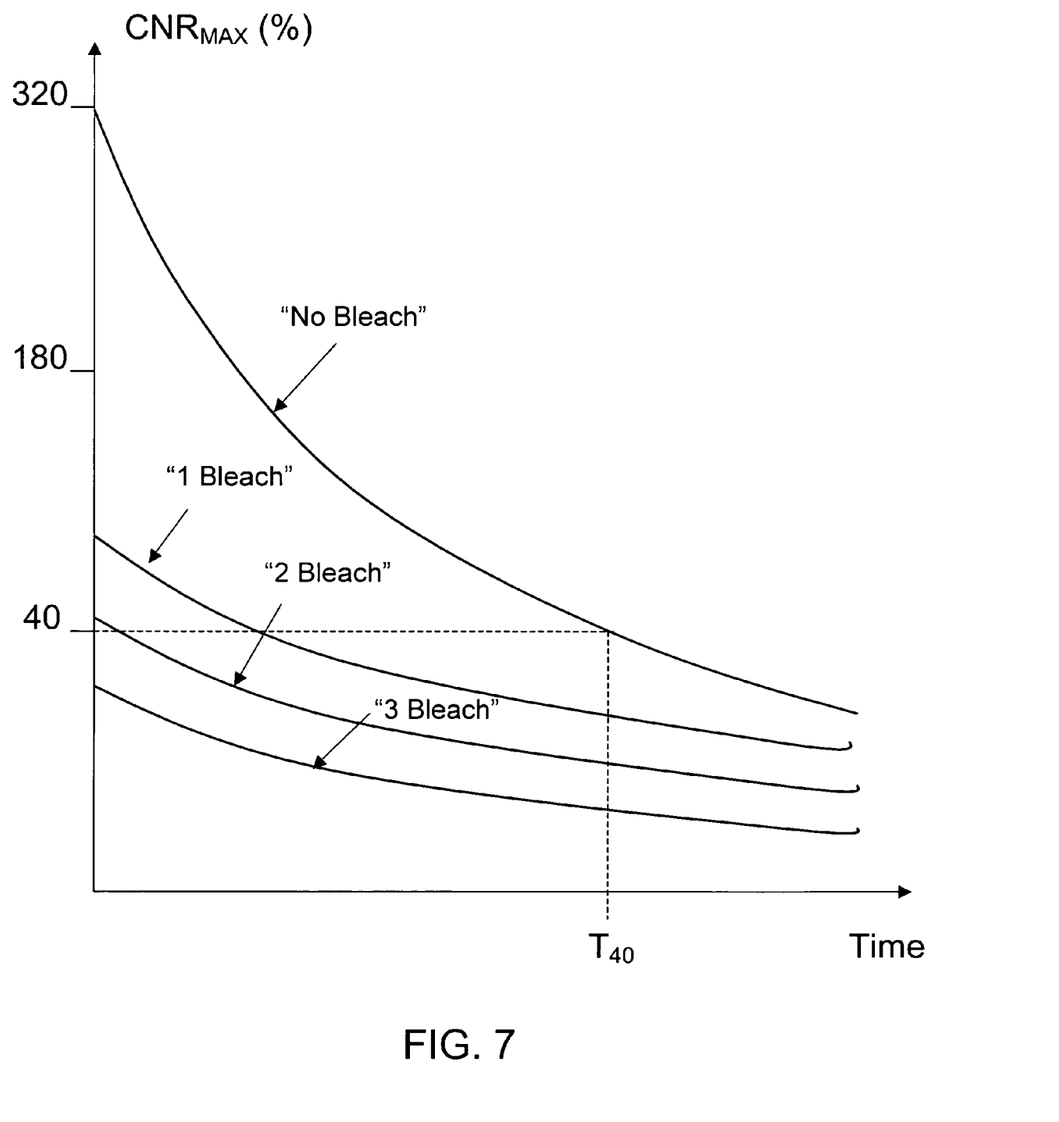
FIG. 7 illustrates a graphical representation of the operation of the scintillator hysteresis detection system in accordance with an embodiment of the present invention.

Similarly, FIG. 7 depicts a second graphical representation of the operation of the scintillator hysteresis detection system 400 used in accordance with an embodiment of the present invention. As opposed to the representation in FIG. 6, $CNR_{max}$ is initially larger in FIG. 7. Therefore, an embodiment of the present invention utilizes a larger bleaching exposure for initially larger $CNR_{max}$. For example, the bleaching exposure may be approximately equivalent to the exposure that caused $CNR_{max}$ to be increased. That is, the bleaching exposure may be approximately equivalent to the exposure that created the possibility of a shape artifact appearing in the image, for example. In addition, the bleaching exposure may alternatively be increased by a factor of 10 or more for an initially larger $CNR_{max}$.

For example, if the initial exposure was 100 mR, then the bleaching exposure may be approximately 100 mR. Alternatively, if the initial exposure was 1000 mR, then the bleaching exposure may be approximately 1000 mR. In addition, if the initial exposure was 100 mR, but an extremely large $CNR_{max}$ was measured, for example, then the bleaching exposure may be increased by a factor of 10 up to approximately 1000 mR.

The curve designated "No bleach" represents a situation where shape artifacts could be visible for a time period $T_{40}$ during which the $CNR_{max}$ is above 40%. Alternatively, if a threshold of $CNR_T$=50% is used, a shape artifact may be visible for a shorter duration than $T_{40}$, while the curve marked "No bleach" remains above a $CNR_{max}$ of 50%.

Conversely, the remaining three curves in FIG. 7 designated as "1 bleach," "2 bleach" and "3 bleach" represent the $CNR_{max}$ over a period of time with "bleaching" of the detector 410, as described above. That is, as opposed to the previous discussion, the curves represent an x-ray system that has determined that $CNR_{max}$ exceeds CNRT and is now "bleaching" the detector 410 with a flat field x-ray dose 450.

The curve designated "1 bleach" represents the $CNR_{max}$ of an image 470 from a detector 410 that has been "bleached" once with a flat field x-ray flux 450 dose of 1000 mR, for example. The curve designated "2 bleach" represents the $CNR_{max}$ of an image 470 from a detector 410 that has been bleached twice with a flat field x-ray flux 450 dose of 1000 mR, for example. The curve designated "3 bleach" represents the $CNR_{max}$ of an image 470 from a detector 410 that has been bleached three times with a flat field x-ray flux 450 dose of 1000 mR, for example.

As previously stated, a $CNR_{max}$ above a $CNR_T$ of 40%, for example, may be representative of a situation in which a shape artifact is visible to the human eye. Therefore, after the possibility for the detector to produce images 470 with shape artifacts is discovered by the data acquisition system 440 of the scintillator hysteresis detection system 400, the possibility of a shape artifact appearing in the image 470 may be reduced or eliminated by a singular or multiple iterations of "bleaching" of the detector 410 with a flat field x-ray flux 450, as described above, for example.

When a $CNR_{max}$ greater than $CNR_T$ is discovered by the data acquisition system 440, the data acquisition system 440 may send exposure communication 480 to the x-ray flux source 420. The exposure communication 480 commands the x-ray flux source 420 to expose the detector 410 to an x-ray flux 450 of 1000 mR, for example. The x-ray flux source 420 then exposes the detector 410 to an x-ray flux 450 of 1000 mR, for example. The curve designated "1 bleach" represents the $CNR_{max}$ of an image 470 from a detector 410 that has been "bleached" once with a flat field x-ray flux 450 dose of 1000 mR, for example.

While the $CNR_{max}$ of the image 470 from a detector 410 may be reduced after the first "bleach" of the detector 410, the $CNR_{max}$ of the image 470 from the detector 410 may remain above $CNR_T$ for a period of time. Therefore, the possibility of a shape artifact being visible in the image 470 can still exist for a period of time. Therefore, after a first "bleach," the x-ray flux source 420 again irradiates the detector 410 with a flat field x-ray flux 450 in order to determine $CNR_{max}$ of the image 470, as described above. After the electronic readout 430 collects the image signals 460, the data acquisition system 440 determines that the $CNR_{max}$ of an image 470 from the detector 410 is initially greater than $CNR_T$. However, the $CNR_{max}$ is still initially greater than $CNR_T$, leaving the possibility for the detector to produce images 470 with shape artifacts. Therefore, the data acquisition system 440 determines that another "bleaching" flat field x-ray dose 450 may be required to further reduce or eliminate the possibility of shape artifact appearing in images 470 from the detector 410.

The data acquisition system 440 then sends exposure communication 480 to the x-ray flux source 420 commanding the x-ray flux source 420 to expose the detector 410 to a second "bleaching" flat field x-ray dose 450 of 1000 mR, for example. The x-ray flux source 420 then exposes the detector 410 to a second x-ray flux 450 of 1000 mR, for example. The effects on the $CNR_{max}$ of an image 470 from the detector 410 after the second detector 410 "bleach" are designated by the curve labeled "2 bleach," for example.

The $CNR_{max}$ of an image 470 from the detector 410 may now be reduced again. After another exposure of the detector 410 to a flat field x-ray flux 450, the data acquisition system 440 determines that the $CNR_{max}$ of an image 470 from the detector 410 is initially greater than $CNR_T$, as shown in the "2 bleach" curve of FIG. 7.

As the $CNR_{max}$ of an image 470 from the detector remains greater than $CNR_T$, the data acquisition system 440 may then send exposure communication 480 to the x-ray flux source 420 commanding the x-ray flux source 420 to expose the detector 410 to a third "bleaching" flat field x-ray dose 450 of 1000 mR, for example. The x-ray flux source 420 then exposes the detector 410 to a third x-ray flux 450 of 1000 mR, for example. The effects on the $CNR_{max}$ of an image 470 from the detector 410 after the third detector 410 "bleach" is shown by the curve labeled "3 bleach," for example.

After another exposure of the detector 410 to a flat field x-ray flux 450, the data acquisition system 440 determines that the $CNR_{max}$ of an image 470 from the detector 410 is less than $CNR_T$. While certain values were associated with the "bleaching" flat field x-ray flux 450 (namely 100 mR and 1000 mR) in FIGS. 6 and 7, for example, these values are merely examples of the operation of the scintillator hysteresis detection system 400.

Alternatively, $CNR_T$ may be adjusted upwards for applications with greater tolerance to shape artifacts. For example, if an application requires a less stringent shape artifact level, the user may increase $CNR_T$. For example, the user may increase $CNR_T$ to 60%. The increase in $CNR_T$ may cause the data acquisition system 440 to take no corrective action when it calculates a $CNR_{max}$ of 55%, for example.

Alternatively, $CNR_T$ may be adjusted downwards for applications that are less tolerant to shape artifacts. For example, if the application is sensitive to very low levels of artifacts, the user may decrease $CNR_T$. For example, the user may decrease $CNR_T$ downwards to 30%. The decrease of $CNR_T$ may cause the data acquisition system 440 to recognize a $CNR_{max}$ of 35% as a level that could produce shape artifacts for the application being used.

Alternatively, the user of the detection system 400 may adjust the size of an ROI. For example, the data acquisition system 440 may contain a user interface so that a user may adjust the size of an ROI. The user may then increase or decrease the size of the ROI, depending on the needs and requirements of the user. For example, the user may increase the ROI from 50 pixels by 50 pixels to 150 pixels by 150 pixels. Alternatively, the user may decrease the ROI for very fine image 470 resolution requirements from 50 pixels by 50 pixels to 25 pixels by 25 pixels, for example.

Alternatively, the user of the scintillator hysteresis detection system 400 may adjust the shape of an ROI. For example, the data acquisition system 440 may contain a user interface so that a user may adjust the shape of an ROI. The user may then increase or decrease the various dimensions of the ROI, depending on the needs and requirements of the user. For example, the user may change the ROI from 50 pixels by 50 pixels to 25 pixels by 100 pixels.

Alternatively, the data acquisition system 440 may automatically alter the size and/or shape of the ROI. For example, the data acquisition system 440 may initially begin with a standard ROI of 50 pixels by 50 pixels. If the data acquisition system 440 detects that $CNR_{max}$ does not exceed $CNR_T$, the data acquisition system 440 may then decrease the ROI size to 40 pixels by 40 pixels for the next analysis of image signals 460, for example. In addition, the data acquisition system 440 may initially begin with a standard ROI shape of 50 pixels by 50 pixels, for example. If the data acquisition system 440 detects that $CNR_{max}$ does not exceed $CNR_T$, the data acquisition system 440 may then alter the ROI shape to 25 pixels by 75 pixels for the next analysis of image signals 460, for example.

Alternatively, the data acquisition system 440 may examine less than the entire image 470 area. For example, there may be a need to focus the analysis of image signals 460 to a particular area of the detector 410. In such a situation, the data acquisition system 440 may be adjusted to examine only the particular area of concern of the detector 410, for example. The data acquisition system 440 may then either discard or ignore image signals 460 for areas outside of the area of concern of the detector 410, for example. Alternatively, the data acquisition system 440 may send image signals 460 to the readout electronics 430 that direct the readout electronics 430 to scan only the particular area of concern of the detector 410.

Alternatively, the data acquisition system 440 does not automatically send exposure communication 480 to the x-ray flux source 420 when $CNR_{max}$ exceeds $CNR_T$. Instead, the data acquisition system 440 may notify a user that the potential for a shape artifact has been discovered. Notification may occur as an audible alarm or a visible warning message on an output of the data acquisition system 440 (for example, on a computer or television screen attached to the data acquisition system 440) or on a warning light on the data acquisition system 440, for example. Thereafter, the user may then direct the data acquisition system 440 to send the exposure communication 480 at a time when the user desires, for example. Once the data acquisition system 440 receives the direction from the user, the data acquisition system 440 may send the exposure communication 480 to the x-ray flux source 420. In this embodiment, the scintillator hysteresis artifact detection system 400 may be employed to detect and reduce or eliminate the possibility of shape artifacts appearing in images 470 at periodic "checkups" of the system 400, for example.

Alternatively, the intensity of the flat field x-ray flux 450 directed by the exposure communication 480 to "bleach" the detector 410 is not fixed to be the same x-ray flux 450 intensity used in initially generating the image 470. Instead, a user of the scintillator hysteresis detection system 400 may set or modify the flat field x-ray flux 450 intensity used in the "bleaching" of the detector 410. In addition, the flat field x-ray flux 450 intensity used in the "bleaching" of the detector 410 may be adjusted for each individual detector 410 "bleach" or the flat field x-ray flux 450 intensity may be set as constant by the user as a fixed value and used for all subsequent detector 410 "bleachings," for example.

Alternatively, the intensity of the flat field x-ray flux 450 directed by the exposure communication 480 to "bleach" the detector 410 changes with time. That is, after the data acquisition system 440 determines that a sufficiently large $CNR_{max}$ exists, the data acquisition system 440 may increase or decrease the flat field x-ray flux 450 intensity with successive "bleachings." That is, for example, if the data acquisition system 440 first discovers a sufficiently large $CNR_{max}$ to possibly create visible shape artifacts in the image 470, the data acquisition system 440 may then send a first exposure communication 480 to the x-ray flux source 420 with a command to "bleach" the detector 410 with a flat field x-ray flux 450. For example, the first exposure communication 480 may command the x-ray flux source 420 to "bleach" the detector 410 with a flat field x-ray flux 450 of 100 mR. Then, if the data acquisition system 440 subsequently discovers that the $CNR_{max}$ of an image 470 has not sufficiently decreased, the data acquisition system 440 may send a second exposure communication 480 to the x-ray flux source 420 with a command to "bleach" the detector 410 with a different flat field x-ray flux 450, for example. The second exposure communication 480 may direct the x-ray flux source 420 to "bleach" the detector 410 with a flat field x-ray flux 450 of 200 mR, for example. The altering of the flat field x-ray flux 450 intensity for subsequent detector 410 "bleachings" may continue until either a user stops the data acquisition system 440 from further altering the flat field x-ray flux 450 intensity, the flat field x-ray flux 450 intensity increases or decreases to a pre-determined limit, the x-ray flux source 420 has "bleached" the detector 410 a number of times that matches or exceeds a pre-determined limit or the data acquisition system 440 determines that the $CNR_{max}$ of an image 470 from the detector 410 has sufficiently decreased, for example.

Alternatively, the x-ray flux source 420 may communicate exposure communication 480 to the data acquisition system 440. The x-ray flux source 420 may communicate the previous x-ray flux 450 "bleaching" level, the number of times the detector 410 has been "bleached," the number of times the detector 410 has been "bleached" with various x-ray flux 450 "bleaching" levels, the time since the last "bleaching" of the detector 410 or any combination of such information, for example. Such communication may be sent at regular intervals, whenever the potential to create a shape artifact is discovered by the data acquisition system 440 or when prompted by a user, for example.

Alternatively, the x-ray flux source 420 irradiates less than the entire surface area of the detector 410. For example, the x-ray flux source 420 may irradiate only a fraction of the entire surface area of the detector 410.

Figure 8:
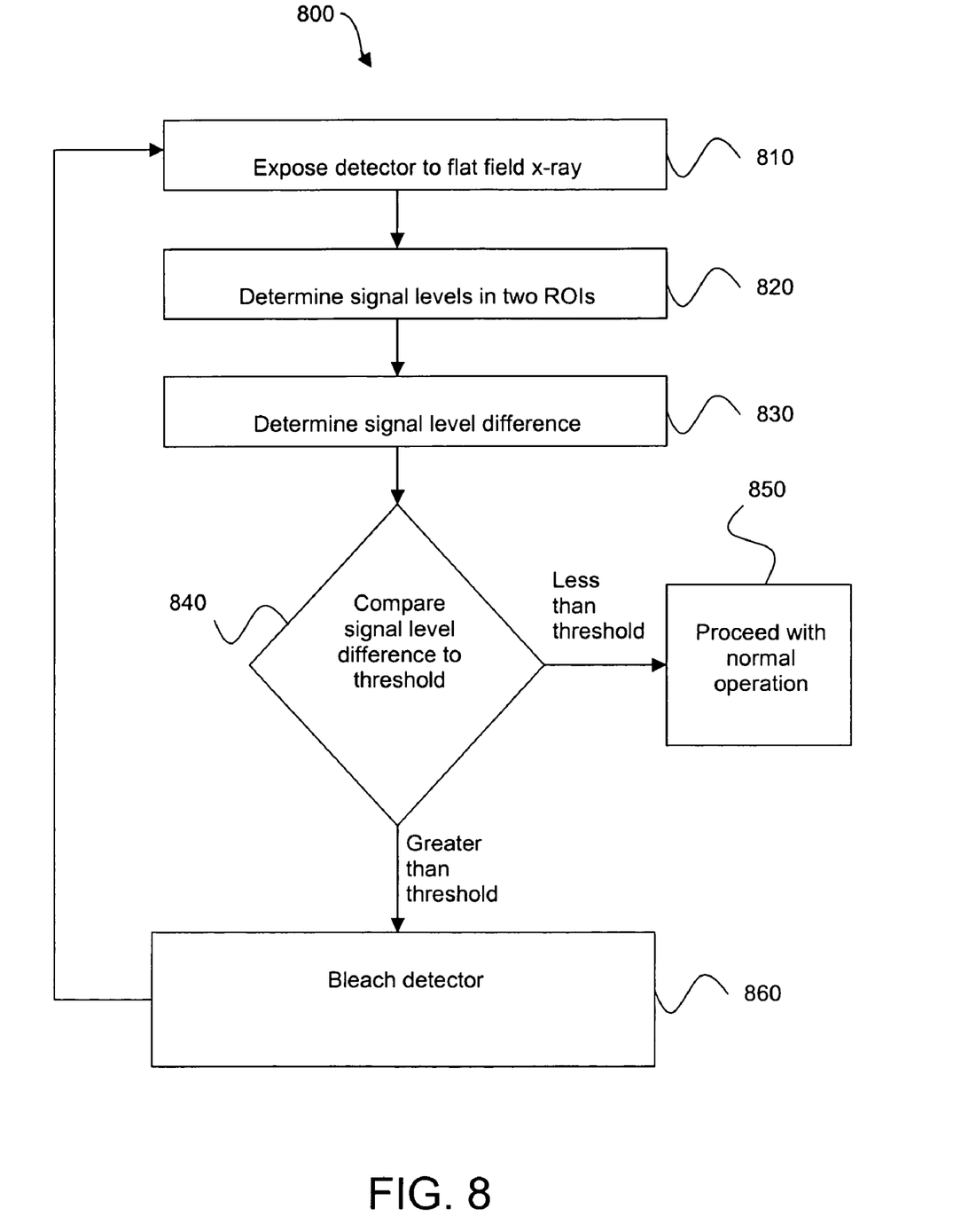
FIG. 8 illustrates a flowchart of an embodiment of the present method for detecting scintillator hysteresis in an x-ray detector in accordance with an embodiment of the present invention.

FIG. 8 illustrates a flowchart 800 of an embodiment of the present method for detecting scintillator hysteresis in an x-ray detector in accordance with an embodiment of the present invention. First, at step 810, a detector is exposed to a flat field x-ray flux. Next, at step 820, signal levels from two ROIs in the detector are determined. That is, the pixels of the detector in two ROIs are scanned to determine the signal levels from the two ROIs.

Next, at step 830, a signal difference between the two ROIs is determined. That is, the signal levels between the two ROIs are compared and a difference between the signal levels of the two ROIs is determined.

Next, at step 840, the signal difference is compared to a threshold. The method 800 determines that the possibility of a shape artifact being visible in the x-ray image exists when the signal difference of the two ROIs is greater than the threshold. The threshold may be a percentage of an average of the standard deviations of the signal levels.

If the signal difference does not exceed the threshold, then the present method proceeds to step 850. At step 850, normal operation of the x-ray detector may proceed as no potential for the detector to produce images with shape artifacts has been discovered.

Conversely, if at step 840 the signal difference is greater than the threshold, the present method 800 proceeds to step 860. At step 860, the detector is irradiated, or "bleached," with a flat field x-ray flux. In one embodiment, the intensity of the flat field x-ray flux is the same x-ray intensity used before the method 800 began at step 810. That is, the x-ray exposure level used to irradiate the detector is the same level that was last used to expose the detector to an x-ray flux.

After the detector has been irradiated with a flat field x-ray flux at step 860, the method 800 proceeds to step 810, where the detector is again exposed to a flat field x-ray exposure. In general, the flat field x-ray exposure at step 810 will be less than the x-ray exposure used in the "bleaching" of the detector at step 860, for example. After the detector has been exposed to the flat field x-ray exposure at step 810, the method 800 continues to step 820, where the signal levels in two ROIs are determined, as described above. In this way, the method proceeds in a loop until the signal level difference between two ROIs is less than the threshold, as described above.

Alternatively, at step 820 the image may be examined to determine signal levels for less than the entire image area. Therefore, the signal levels for less than the entire image area are determined, allowing for the analysis of signal level differences in a portion or section of the x-ray image.

Alternatively, at step 820 the ROIs may be of different image areas. That is, the signal levels are determined for ROIs with different areas.

Alternatively, at step 860 the detector may be "bleached" more than once. That is, at step 860 the detector may be "bleached" multiple times to further ensure that any scintillator hysteresis artifacts are eliminated.

Alternatively, at step 860 a different amount of "bleaching" x-ray exposure intensity may be used. That is, the "bleaching" x-ray exposure intensity can differ from the x-ray exposure intensity used at step 810.

Alternatively, at step 860 the "bleaching" x-ray exposure intensity may be altered depending on the number of times the detector has been "bleached." That is, the "bleaching" x-ray exposure intensity may increase or decrease with each subsequent detector "bleaching."

Alternatively, the method 800 proceeds in a loop until a pre-determined number of "bleaching" x-ray exposures of the detector have occurred. That is, the method 800 proceeds until either the signal difference is less than the threshold at step 840 or the detector has been "bleached" a given number of times at step 860. For example, the method 800 may continue to determine that the signal difference between two ROIs is greater than the threshold (step 840) and "bleach" the detector (step 860) up to 10 times. At that point, for example, the method 800 terminates, for example.

While particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for detecting scintillator hysteresis artifacts in an image from an x-ray detector, said method including:
   examining an image from an x-ray detector to measure a first signal level for a first area of interest and a second signal level for a second area of interest,
   wherein said first area of interest includes a first image area and said second area includes a second image area;
   using a data acquisition system to determine a difference in said first signal level and said second signal level; and
   using the data acquisition system to compare said difference to a threshold to detect a shape artifact from a prior image due to scintillator hysteresis, wherein said shape artifact results from an area of trapped electrical charge in a scintillator.

2. The method of claim 1, further including exposing said x-ray detector with a flat field x-ray exposure to produce said image.

3. The method of claim 1, wherein said first image area differs from said second image area.

4. The method of claim 1, wherein said detector includes a plurality of pixels, said plurality of pixels comprising a first set of pixels and a second set of pixels,
   wherein said first set of pixels are examined to measure a first set of pixel signals and said second set of pixels are examined to measure a second set of pixel signals,
   wherein said first signal level includes said first set of pixel image signals and said second signal level includes said second set of pixel image signals.

5. The method of claim 4, wherein said first set of pixels includes a first plurality of photodiodes, said first plurality of photodiodes measuring said first set of pixel signals and said second set of pixels includes a second plurality of photodiodes, said second plurality of photodiodes measuring said second set of pixel signals.

6. The method of claim 5, wherein said first set of pixel signals is measured by determining an amount of electrical charge discharged in said first plurality of photodiodes and said second set of pixel signals is determined by measuring an amount of electrical charge discharged in said second plurality of photodiodes.

7. The method of claim 4, wherein said threshold is a percentage of an average of a plurality of standard deviations of said first set of pixel image signals and said second set of pixel image signals.

8. The method of claim 1, further including:
   irradiating said detector with an x-ray flux when said difference is greater than said threshold.

9. The method of claim 8, wherein said irradiating step is automatic.

10. The method of claim 2, further including:
    irradiating said detector with an x-ray flux when said difference is greater than said threshold, wherein said x-ray flux is equivalent to said flat field x-ray exposure.

11. The method of claim 2, further including:
    irradiating said detector with an x-ray flux when said difference is greater than said threshold, wherein said x-ray flux is greater than said flat field x-ray exposure.

12. A system for detecting scintillator hysteresis artifacts in images from an x-ray detector, said system including:
    an x-ray image including a first area of interest and a second area of interest,
    wherein said first area of interest has a first signal level and said second area of interest has a second signal level;
    readout electronics measuring said first signal level and said second signal level; and
    a data acquisition system determining a difference between said first signal level and said second signal level,
    wherein said difference is compared to a threshold to detect a shape artifact from a prior image due to scintillator hysteresis, wherein said shape artifact results from an area of trapped electrical charge in a scintillator.

13. The system of claim 12, further including an x-ray detector, wherein said detector is exposed to a flat field x-ray exposure to produce said image.

14. The system of claim 12, wherein said first area differs from said second area.

15. The system of claim 12, further including an x-ray detector exposed to an x-ray flux, said x-ray detector comprising a plurality of pixels, said pixels comprising a first set of pixels and a second set of pixels,
    wherein said first set of pixels are examined to measure a first set of pixel signals and said second set of pixels are examined to measure a second set of pixel signals,
    wherein said first signal level includes said first set of pixel image signals and said second signal level includes said second set of pixel image signals.

16. The system of claim 15, wherein said first set of pixels includes a first plurality of photodiodes and said second set of pixels includes a second plurality of photodiodes,
    said first plurality of photodiodes measuring said first set of pixel signals and said second set of pixels includes a second plurality of photodiodes, said second plurality of photodiodes measuring said second set of pixel signals.

17. The system of claim 16, wherein said readout electronics measure said first set of pixel signals by scanning a first amount of electrical charge discharged in said first plurality of photodiodes and said second set of pixel signals by scanning a second amount of electrical charge discharged in said second plurality of photodiodes.

18. The system of claim 15, wherein said threshold is a percentage of an average of a plurality of standard deviations of said first set of pixel image signals and said second set of pixel image signals.

19. The system of claim 15, further including:
    an x-ray flux source irradiating said detector with a second x-ray flux when said difference is greater than said threshold.

20. The system of claim 19, wherein said x-ray flux source automatically irradiates said detector.

21. The system of claim 13, further including:
    an x-ray flux source irradiating said detector with a second x-ray flux when said difference is greater than said threshold, wherein said second x-ray flux is equivalent to said flat field x-ray exposure.

22. The system of claim 13, further including:
    an x-ray flux source irradiating said detector with a second x-ray flux when said difference is greater than said threshold, wherein said second x-ray flux is greater than said flat field x-ray exposure.

* * * * *